US006938883B2

(12) United States Patent
Adams et al.

(10) Patent No.: US 6,938,883 B2
(45) Date of Patent: Sep. 6, 2005

(54) GUIDE FOR SELECTIVELY RECEIVING A WICK IN A DISPENSER FOR A VOLATILE LIQUID

(75) Inventors: Mary Beth Adams, Antioch, IL (US); Ralph Schwarz, Racine, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

(21) Appl. No.: 10/607,777

(22) Filed: Jun. 27, 2003

(65) Prior Publication Data

US 2004/0262788 A1 Dec. 30, 2004

(51) Int. Cl.[7] ................................................. B01F 3/04
(52) U.S. Cl. ................. 261/30; 261/107; 261/DIG. 88; 422/124; 239/44
(58) Field of Search ................. 261/30, 104, 107, 261/DIG. 88; 422/124; 239/44

(56) References Cited

U.S. PATENT DOCUMENTS

| | | | | |
|---|---|---|---|---|
| 1,911,871 A | * | 5/1933 | Anderson | 422/124 |
| 2,435,811 A | | 2/1948 | Waters | 240/10 |
| 2,557,501 A | | 6/1951 | Fusay et al. | 21/119 |
| 2,764,789 A | | 10/1956 | Zelenka | 21/74 |
| 2,828,953 A | | 4/1958 | Hartmann | 261/30 |
| 3,080,624 A | | 3/1963 | Weber III | 21/120 |
| 3,587,968 A | | 6/1971 | Balland et al. | 239/47 |
| 3,748,464 A | | 7/1973 | Andeweg | 240/108 R |
| 3,749,904 A | | 7/1973 | Graff | 240/10 B |
| 3,761,702 A | | 9/1973 | Andeweg | 240/2 R |
| 3,790,081 A | | 2/1974 | Thornton et al. | |
| 3,890,085 A | | 6/1975 | Andeweg | 431/125 |
| 3,923,458 A | | 12/1975 | Moran | 21/74 R |
| 3,948,445 A | | 4/1976 | Andeweg | 239/53 |
| 3,990,848 A | | 11/1976 | Corris | |
| 3,993,444 A | | 11/1976 | Brown | |
| 4,035,451 A | | 7/1977 | Tringali | |

(Continued)

FOREIGN PATENT DOCUMENTS

| | | |
|---|---|---|
| AU | 664685 | 11/1995 |
| DM | DM/054926 | 9/2000 |
| EP | 0 882 459 | 12/1998 |
| EP | 1 031 446 | 8/2000 |
| EP | 1 270 021 | 1/2003 |
| EP | 1 392 368 | 10/2003 |
| EP | 1 283 062 A1 | 12/2003 |
| GB | 2285579 | 7/1995 |
| WO | WO 95/10352 | 4/1995 |
| WO | WO 01/02025 A1 | 1/2001 |
| WO | WO 01/23008 A1 | 4/2001 |
| WO | WO 02/30220 A1 | 4/2002 |
| WO | WO 02/31413 A2 | 4/2002 |
| WO | WO 03/013618 | 2/2003 |
| WO | WO03/086487 | 10/2003 |
| WO | WO 2004/030708 | 4/2004 |

OTHER PUBLICATIONS

International Search Report and Written Opinion for Appl. No. PCT/US2004/020591.

"Inglow™Candle Company" www.inglowcandle.com (2002).

"Luna Candles" http://www.epartyunlimited.com/luna-candles.html (print date 2005).

International Search Report and Written Opinion, Aug. 16, 2004, Appl. No. PCT/US04/008436.

International Search Report and Written Opinion, Aug. 16, 2004, Appl. No. PCT/US04/008437.

*Primary Examiner*—Robert A. Hopkins

(57) ABSTRACT

A dispenser for a volatile liquid includes a housing and a fan mounted in the housing for generating an air stream. A guide associated with the housing and defines an opening having predetermined dimension to selectively receive a wick and to position the wick in alignment with the fan to immerse the wick into an air stream when the fan is actuated.

52 Claims, 3 Drawing Sheets

U.S. PATENT DOCUMENTS

| | | | |
|---|---|---|---|
| 4,166,087 A | 8/1979 | Cline et al. | |
| 4,276,236 A | 6/1981 | Sullivan et al. | |
| 4,294,778 A | 10/1981 | DeLuca | |
| 4,323,193 A | 4/1982 | Compton et al. | |
| 4,346,059 A | 8/1982 | Spector | 422/125 |
| 4,383,951 A | 5/1983 | Palson | |
| 4,432,938 A | 2/1984 | Meetze, Jr. | |
| 4,493,011 A | 1/1985 | Spector | 362/96 |
| 4,621,768 A | 11/1986 | Lhoste et al. | 239/44 |
| 4,660,764 A | 4/1987 | Joyaux et al. | 239/44 |
| 4,666,638 A | 5/1987 | Baker et al. | |
| 4,695,435 A | 9/1987 | Spector | |
| 4,707,338 A | 11/1987 | Spector | |
| 4,739,928 A | 4/1988 | O'Neil | |
| 4,743,406 A | 5/1988 | Steiner et al. | |
| 4,857,240 A | 8/1989 | Kearnes et al. | |
| 4,866,580 A | 9/1989 | Blackerby | 362/205 |
| 4,913,350 A | 4/1990 | Purzycki | 239/44 |
| 4,931,224 A | 6/1990 | Holzner, Sr. | |
| 4,968,487 A | 11/1990 | Yamamoto et al. | 422/125 |
| RE33,864 E | 3/1992 | Steiner et al. | |
| 5,095,647 A | 3/1992 | Zobele et al. | 43/125 |
| 5,114,625 A | 5/1992 | Gibson | |
| 5,126,078 A | 6/1992 | Steiner et al. | |
| 5,133,042 A | 7/1992 | Pelonis | |
| 5,217,696 A | 6/1993 | Wolverton et al. | 422/121 |
| 5,223,182 A | 6/1993 | Steiner et al. | |
| 5,342,584 A | 8/1994 | Fritz et al. | |
| 5,370,829 A | 12/1994 | Kunze | |
| 5,376,338 A | 12/1994 | Zlotnik | |
| 5,547,616 A | 8/1996 | Dancs et al. | |
| 5,647,053 A | 7/1997 | Schroeder et al. | |
| 5,651,942 A | 7/1997 | Christensen | 422/125 |
| 5,662,835 A | 9/1997 | Collingwood | |
| D386,974 S | 12/1997 | Wefler | |
| D393,063 S | 3/1998 | Wefler | |
| 5,891,400 A | 4/1999 | Ansari et al. | 422/125 |
| 5,909,845 A | 6/1999 | Greatbatch et al. | |
| 5,970,643 A | 10/1999 | Gawel, Jr. | |
| 5,980,064 A | 11/1999 | Metroyanis | 362/194 |
| 6,017,139 A | 1/2000 | Lederer | 362/394 |
| 6,104,867 A | 8/2000 | Stathakis et al. | 392/403 |
| 6,106,786 A | 8/2000 | Akahoshi | 422/124 |
| 6,196,706 B1 | 3/2001 | Cutts | 362/392 |
| 6,354,710 B1 | 3/2002 | Nacouzi | 362/96 |
| 6,361,752 B1 | 3/2002 | Demarest et al. | 422/306 |
| 6,371,450 B1 | 4/2002 | Davis et al. | |
| 6,454,425 B1 | 9/2002 | Lin | 362/96 |
| 6,484,438 B2 | 11/2002 | Matsunaga et al. | 362/96 |
| 6,555,068 B2 | 4/2003 | Smith | |
| 6,616,308 B2 | 9/2003 | Jensen et al. | 362/351 |
| 6,619,560 B1 | 9/2003 | Chun | 239/44 |
| 2002/0080601 A1 | 6/2002 | Meltzer | 362/96 |
| 2002/0093834 A1 | 7/2002 | Yu et al. | 362/565 |
| 2002/0136542 A1 | 9/2002 | He et al. | 392/395 |
| 2002/0136886 A1 | 9/2002 | He et al. | 428/313.5 |
| 2003/0007887 A1 | 1/2003 | Roumpos et al. | 422/1 |
| 2003/0053305 A1 | 3/2003 | Lin | 362/96 |
| 2003/0146292 A1 | 8/2003 | Schramm et al. | |
| 2004/0141315 A1 | 7/2004 | Sherburne | 362/161 |
| 2004/0246711 A1 | 12/2004 | Brenchley et al. | 362/161 |

* cited by examiner

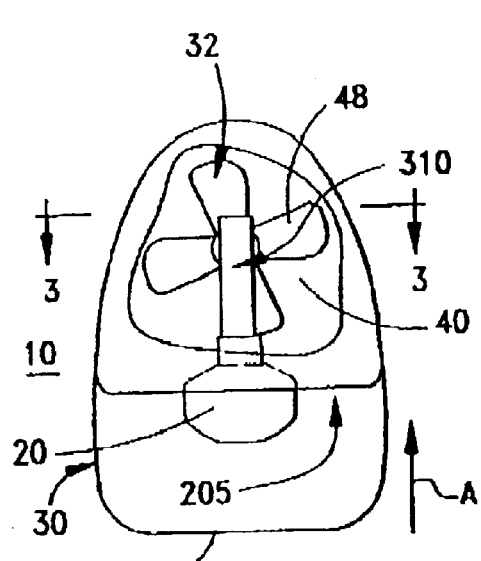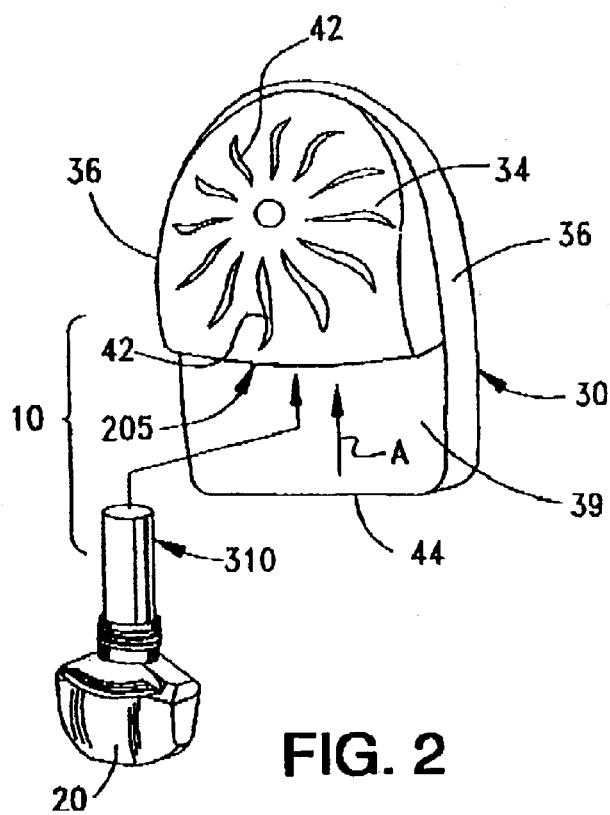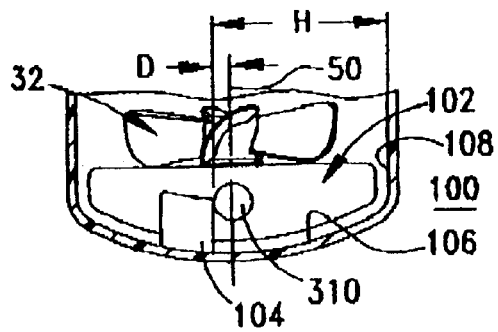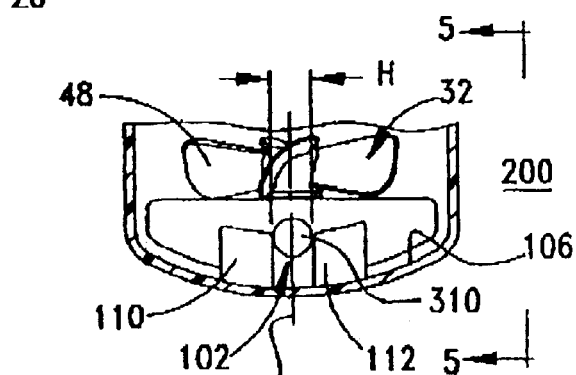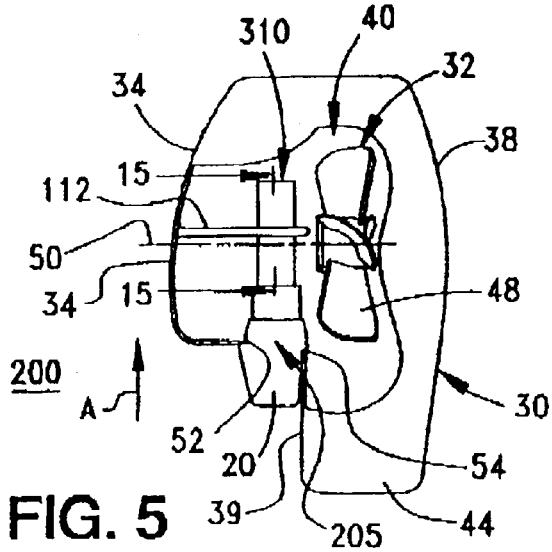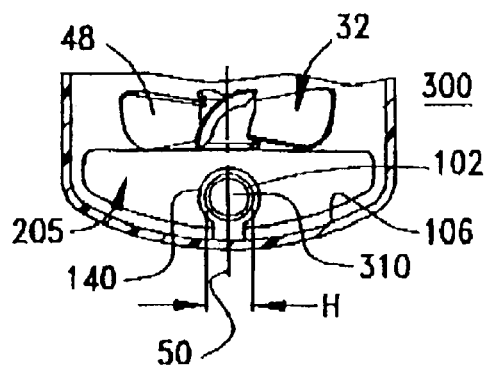

GUIDE FOR SELECTIVELY RECEIVING A WICK IN A DISPENSER FOR A VOLATILE LIQUID

FIELD OF THE INVENTION

The present invention relates to dispensing systems for volatile liquids and, more particularly, to wick-based dispensers.

BRIEF DESCRIPTION OF THE DRAWINGS

FIG. 1 is a front schematic elevational view with the housing of the dispenser partially cut away (without a guide showing);

FIG. 2 is a perspective view showing insertion of a wick into a housing of a dispensing device of the present invention;

FIG. 3 is a cross-sectional partially cut away view of the dispenser of FIG. 1 taken along line 3—3 of the present invention in which an embodiment of a guide is shown;

FIG. 4 is a cross-sectional partially cut away view of the dispenser of FIG. 1 taken along line 3—3 of the present invention in which a second embodiment of the guide is shown;

FIG. 5 is a partially cut away side elevational view of the second embodiment of the present invention shown in FIG. 4;

FIG. 6 is a cross-sectional partially cut away view of the dispenser of FIG. 1 taken along line 3—3 of the present invention in which a third embodiment of the guide is shown;

DETAILED DESCRIPTION OF THE INVENTION

Figure 7:
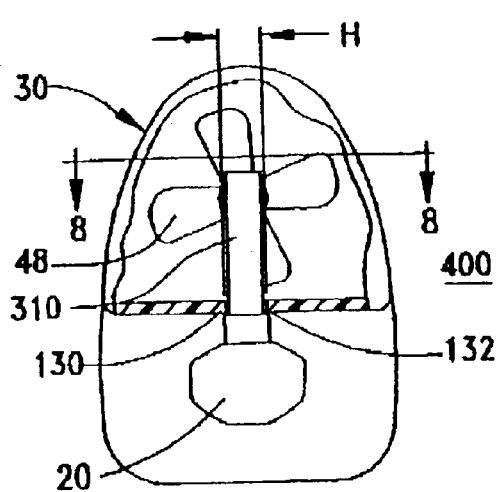
FIG. 7 is a front elevational view of the dispenser of FIG. 1 showing a fourth embodiment of the guide of the present invention.

Referring to FIGS. 1 and 2, volatile liquid dispenser 10 is designed to disseminate a volatile liquid, such as a fragrance compound, into a room. The fragrance compound is disseminated via a forced air stream flowing around a wick 310 at room ambient temperature. According to the present invention, dispenser 10 includes a housing 30, a motorized fan 32 mounted in housing 30 for generating an air stream, and a wick 310 coupled to housing 30 by way of container 20, which holds the volatile liquid releasably engaging dispenser 10.

As seen in FIG. 2, housing 30 includes a front wall 34, a side 36 formed at each lateral end of front wall 34, and a rear wall 38 formed opposite front wall 34. Front wall 34, sides 36, and rear wall 38 combine to form an enclosure 40, as seen in FIG. 1, for housing fan 32 and for receiving wick 310 into the air stream generated by fan 32.

Front wall 34 is generally spaced apart from base front wall 39, as seen in FIGS. 2 and 5, which permits access into enclosure 40 for wick 310 and will provide releasable securement of container 20 which will be discussed in more detail below. One or more air inlet ports (not shown) may be formed in rear wall 38 for providing intake air for fan 32. Also, one or more air outflow ports 42 are provided in front wall 34, as seen in FIG. 2, to provide a path for outflow of the air stream conveying the fragrance compound which has evaporated in the air stream to pass from enclosure 40 into the room dispenser 10 is located.

A lower portion of housing 30 forms a base 44, as seen in FIGS. 1 and 2, configured to enable dispenser 10 to rest on a flat surface such as a shelf or table. A switch or button (not shown) may be provided on an exterior surface of housing 30 to enable activation and deactivation of the fan motor.

Referring to FIGS. 1 and 5, fan 32 is powered by a battery (not shown) positioned in base 44 of housing 30. Access to the battery may be provided by a hinged or removable access plate formed in base 44. Fan 32 includes a plurality of fan blades 48 that rotate about a fan axis of rotation 50, as seen in FIG. 5, during operation of the fan.

Referring now to FIG. 1, wick 310 is to be positioned and secured in enclosure 40 formed by housing 30 and so as to reside in the air stream generated by fan 32. Wick 310 may be secured in the desired position by coupling wick 310 to dispenser housing 30 using any one of numerous methods of securement.

In one example (FIG. 5) wick 310 is secured in a container 20 holding the volatile liquid to be dispensed. A portion of wick 310 is in communication with the volatile liquid in container 20. Another portion of wick 310 extends outside container 20 for immersion into the air stream. Dispenser housing 30 has opposing sidewalls 34 and 39. Each of opposing sidewalls 34 and 39 has a corresponding edge portion 52 and 54, respectively. Edge portions 52, 54 define an opening adapted to receive wick 310 and a portion of container 20 into enclosure 40. A retention structure is formed along one or more of opposing sides of container 20 to help position and releasably secure container 20 between opposing sidewalls 34 and 39 of housing 30. The retention structure may be formed integral with container 20 such as detents or grooves formed into the container whereby the detents or grooves engage edge portions 52, 54 thereby releasably securing container 20 to housing 30. When container 20 is secured to dispenser housing 30 as described above, wick 310 is positioned in the air stream generated by fan 32.

In an alternative embodiment (not shown), a receptacle for wick 310 may be formed on dispenser housing 30 for positioning of wick 310 directly into interior 40 and in alignment with the fan and immersed into an air stream generated by the fan. In addition, any one of several other alternative embodiments (not shown) may be used to position and releasably secure container 20 holding wick 310 to housing 30 including utilizing contact adhesives, hook loop fasteners, interference fit of the container to housing 30 and the like.

Referring now to FIGS. 3–12, various embodiments of a guide, generally designated 100, 200, 300, 400, 500, 600 and 700, may be associated with housing 30 to define an opening 102 having a predetermined dimension H to selectively receive wick 310 therein. As seen in FIGS. 3–12, predetermined dimension H of opening 102 may be oriented generally transverse to fan axis of rotation 50. In a manner to be described later, wick 310 is selectively received in opening 102 based on a dimension of the wick relative to predetermined dimension H of opening 102. As seen in FIG. 3, guide 100 is positioned in association with housing 30 such that when wick 310 is selectively received in opening 102, guide 100 effectively positions a portion of wick 310 extending therethrough in alignment with fan 32 to immerse wick 310 into an air stream when fan 32 is activated. Guide 100 may either be formed integral with housing 30 or formed as one or more separate components which are then coupled to housing 30.

In a number of the embodiments described herein, wick 310 is to be inserted into housing opening 205 in a direction indicated by arrow "A", FIGS. 1, 2 and 5. Otherwise, other securements as mentioned above may be employed to secure container 20 to housing 30. Also, as seen in the various guide embodiments described below, opening 102 is positioned to receive wick 310 therein to align wick 310 with fan rotational axis 50.

Referring to FIG. 3, in a first embodiment, guide 100 comprises a projection 104 extending from a surface 106 of housing 30 and positioned spaced apart from another surface 108 of housing 30. In this embodiment, opening 102 defined by guide 100 is the space between projection 104 and other housing surface 108, and the predetermined dimension H is the separation distance between projection 104 and other housing surface 108.

In FIG. 3, projection 104 may be spaced apart from fan rotational axis 50 in a direction transverse to a direction indicated by arrow "A" (FIG. 1), in which the wick is received into opening 102. In this embodiment, in which a single projection 104 is used to define opening 102, the distance D of projection 104 from fan rotational axis 50 is controlled so that a wick 310 may be selectively received which has a diameter W (FIG. 15) less than or equal to approximately 2D when wick 310 is positioned in enclosure 40 such that longitudinal axis 60 of wick 310 is in line with fan rotational axis 50. As seen in FIGS. 3–6 and 11, the wick dimension W (FIG. 15) may be oriented generally transverse to fan axis of rotation 50.

In the embodiment shown in FIG. 3, projection 104 is positioned in an interior portion of housing 30, in the air stream generated by fan 32. Alternatively, projection 104 could be positioned on an exterior surface of housing 30.

Referring to FIGS. 4 and 5, in a second embodiment guide 200 comprises two spaced apart projections 110 and 112 extending from a surface 106 of housing 30. Projections 110 and 112 may each be similar in structure to single projection 104 in first guide embodiment 100 described above. In this embodiment, the opening 102 defined by guide 200 is the space between projections 110 and 112, and the predetermined dimension H is the separation distance between projections 110 and 112.

As seen in FIGS. 4 and 5, projections 110 and 112 may be positioned in an interior portion of housing 30 so as to reside in the air stream generated by fan 32 when the fan is in operation. In this configuration, projections 110 and 112 can be relatively thin along wick insertion direction "A" and will have relatively smooth edges and surfaces, for minimizing turbulence and air resistance caused by positioning of projections 110 and 112 in the air stream.

In other embodiments (not shown), projections 110 and 112 can be positioned on an exterior surface of housing 30, or spaced apart projections 110 and 112 may be positioned at an entrance to the opening 205 leading into the interior of housing 30.

Referring to FIG. 6, in a third embodiment guide 300 may comprise a wall member 140 positioned along an interior surface 106 of housing 30 and structured so as to either partially or entirely surround opening 102 into which wick 310 extends. The embodiment of guide 300 shown in FIG. 6 then receives wick 310 therein and partially or completely surrounds a portion of the length of wick 310.

Figure 8:
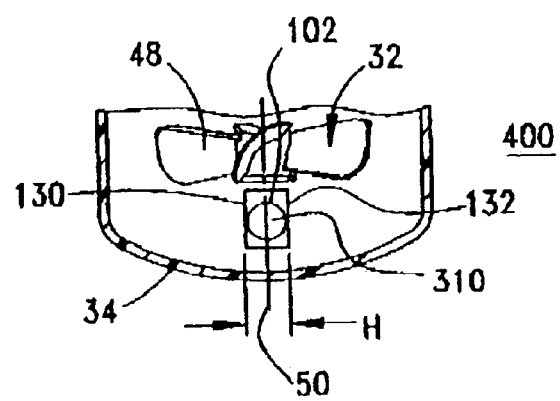
FIG. 8 is a cross-sectional view of the dispenser of FIG. 7 taken along line 8—8 of the present invention in which the fourth embodiment of the guide is shown.
Figure 9:
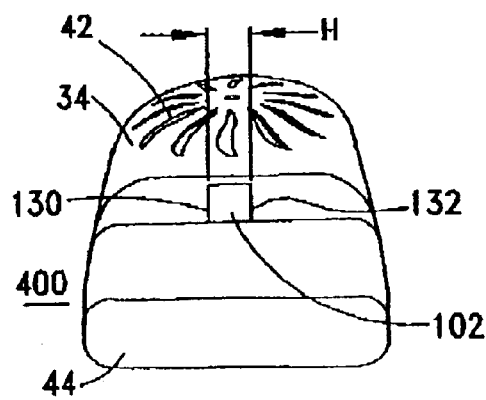
FIG. 9 is a bottom perspective view of the fourth embodiment of the dispenser of the present invention of FIG. 7 without the container and wick.

Referring to FIGS. 7, 8 and 9, a fourth embodiment of guide 400 comprises a pair of opposing sidewalls 130 and 132 formed in housing 30 and defining opening 102 into the interior portion of housing 30. In this embodiment, predetermined dimension H is defined by the spacing between sidewalls 130 and 132. In this embodiment container 20 may be secured to housing 30 with the employment of a contact adhesive or hook loop fasteners (not shown).

Figure 10:
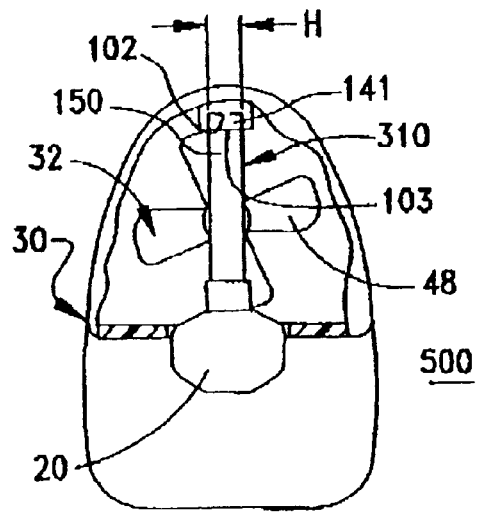
FIG. 10 is a front schematic elevational view of the dispenser of FIG. 1 showing a fifth embodiment of the guide of the dispenser of the present invention.

Referring to FIG. 10, in a fifth embodiment guide 500 includes a wall member 141 and an opening 102 defined therein. Wall member 141 may be positioned in association with housing 30 such that opening 102 receives a top portion 150 of wick 310 when the wick is secured to housing 30.

Figure 11:
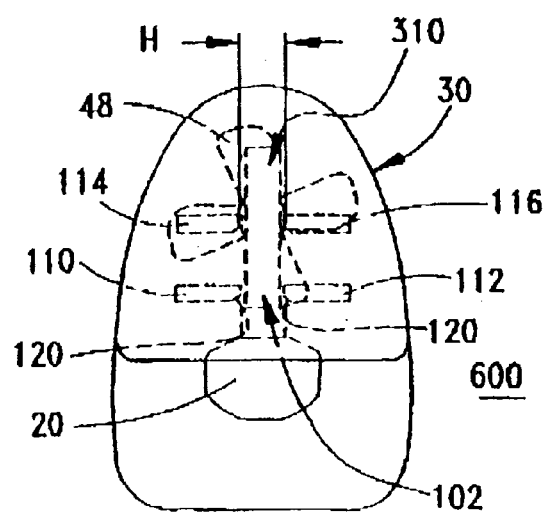
FIG. 11 is a front schematic elevational view of a sixth embodiment of the guide (shown in phantom without outlet vents shown in the front wall of the dispenser) of the present invention.

Referring to FIG. 11, in a sixth embodiment, guide 600 includes at least two sets of spaced apart projections 110,112 and 114, 116 similar to those described above, each set being spaced apart from the other and in this example secured to an interior wall of housing 30 including front wall 34. This arrangement, in which projections 110, 112, 114 and 116 are positioned proximate multiple points along either side of the length of wick 310, may provide added stability to a wick inserted between the spaced apart projections. Also, as seen in FIG. 11, a chamfer 120 may be provided along each edge of projections 110 and 112 residing nearest opening 102 to aid in directing wick 310 into and through opening 102.

Figure 12:
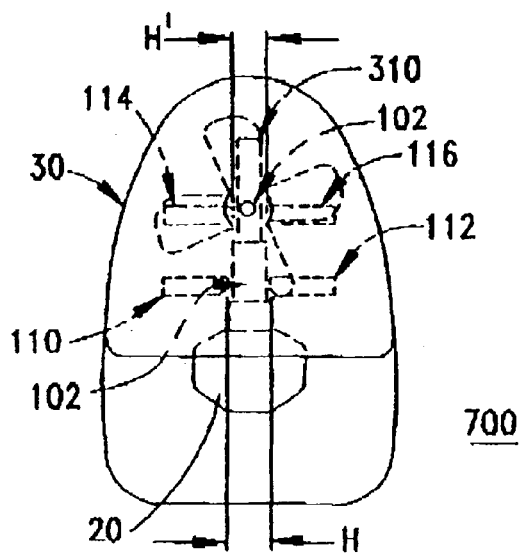
FIG. 12 is a front schematic elevational view of a seventh embodiment of the guide (shown in phantom without outlets shown in the front wall of the dispenser) of the present invention.

Referring to FIG. 12, in a seventh embodiment of guide 700 (a variation of the embodiment shown in FIG. 11), a separation H' between spaced apart projections 114 and 116 residing farther along the path of insertion of wick 310 may be less than the separation distance H between projections 110 and 112 between which wick 310 is first inserted. In this respect, second set of projections 114 and 116 defines a second opening 102 having a second pre-determined dimension H' to selectively receive and to position a portion of wick 310 in alignment with fan 32. This arrangement enables a "stepped wick", as seen in FIG. 12, or a tapered wick (not shown) to be selectively received between two sets of spaced apart projections 110, 112 and 114, 116.

Figure 13:
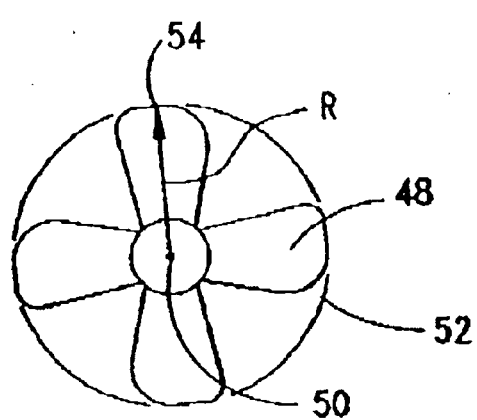
FIG. 13 is a schematic front elevational view of a fan of the present invention as shown in FIG. 1 with an outline demarking the sweep of the radius of a blade.
Figure 14:
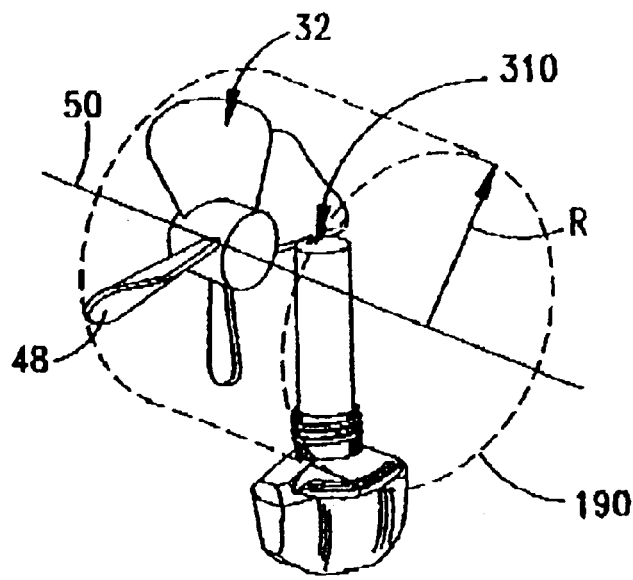
FIG. 14 is a schematic perspective view showing the positioning of the wick in a cylindrical volume defined by a fan mounted in the dispenser housing.

Referring to FIGS. 13 and 14, for purposes of positioning wick 310 in the air stream generated by fan 32, a cylindrical volume 190 is defined which is centered along fan axis of rotation 50 and which has a radius R that extends from axis of rotation 50 to an edge 54 of the fan blade farthest from fan rotational axis 50. During rotation, fan blades 48 trace out a circumferential path 52. As shown in FIG. 13, fan blades 48 each have a dimension R extending from axis of rotation 50 to an edge 54 of the respective fan blade 48 farthest from axis of rotation 50. As it is desired for wick 310 to be positioned in the air stream generated by fan 32, any embodiment of guide 100 will generally be positioned such that opening 102 defined by guide 100 receives wick 310 therein to position at least a portion of wick 310 within cylindrical volume 190.

Figure 15:
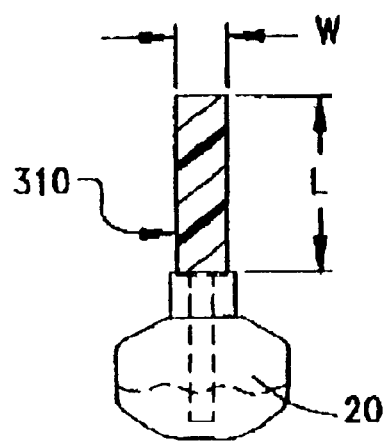
FIG. 15 is a front elevational view of the wick and container which includes the wick in cross section taken along lines 15—15 as shown in FIG. 5.

In general, predetermined dimension H of opening 102 will be greater than a corresponding dimension W of wick 310, shown in FIG. 15. In addition, in any one of the embodiments described above, predetermined dimension H may be defined with respect to a dimension of fan 32. For example, referring to FIG. 13, where a blade 48 of fan has a length R measured from fan axis of rotation 50 to the edge 54 of the fan blade farthest away from the axis, predetermined dimension H is defined so as not to exceed 1.25 R. In alternative embodiments, predetermined dimension H may be defined so as not to exceed 1.1 R, 0.9R, or any other pre-determined lesser multiple of R.

Also, in referring to FIG. 15, wick dimension W may be correspondingly defined with respect to fan blade dimension R such that a slight clearance fit is provided between wick 310 and portions of guide 100–700 defining opening 102. For example, when predetermined dimension H is defined so as to not exceed 1.25R, wick dimension W will be defined so as to not exceed 1.2 R. The various guide embodiments and the dimension H between the guide structures limits the dimension W of a wick which can be placed into the air stream of the fan.

INDUSTRIAL APPLICABILITY

The present invention provides a structure and method for ensuring reliable placement of a wick in a desired position and orientation in an air stream generated by a fan mounted in a housing of a dispenser for volatile liquids. The structure also enables control of the size and/or configuration of a wick insertable into the air stream.

It should be understood that the preceding is merely a detailed description of various embodiments of this invention and that numerous changes to the disclosed embodiment can be made in accordance with the disclosure herein without departing from the spirit or scope of the invention. The preceding description, therefore, is not meant to limit the scope of the invention. Rather, the scope of the invention is to be determined only by the appended claims and their equivalents.

What is claimed is:

1. A dispenser for a volatile liquid, comprising:
 a housing;
 a fan mounted to the housing to generate an air stream;
 a guide including a projection disposed on an inside surface of the housing provides at least one boundary in defining an opening in which the opening has a predetermined dimension to selectively receive a wick and to position the wick in alignment with the fan to immerse the wick into an air stream when the fan is activated.

2. The dispenser of claim 1, wherein the guide comprises two spaced apart projections extending from a surface of the housing.

3. The dispenser of claim 2, wherein the two projections are positioned in an interior portion of the housing.

4. The dispenser of claim 2, wherein the two projections extend in the general direction of the air stream generated by the fan.

5. The dispenser of claim 4, wherein the predetermined dimension is the distance between the two projections.

6. The dispenser of claim 2, wherein the guide includes a second set of spaced apart projections in which the two spaced apart projections and the second set of projections are spaced apart from one another.

7. The dispenser of claim 6, wherein the second set of spaced apart projections defines a second opening having a second pre-determined dimension to selectively receive and to position a portion of the wick in alignment with the fan.

8. The dispenser of claim 2, wherein the two spaced apart projections are positioned at an entrance of another opening defined in the housing.

9. The dispenser of claim 2, wherein the projections are positioned in the air stream generated by the fan.

10. The dispenser of claim 2, wherein the projection is positioned in an interior portion of the housing.

11. The dispenser of claim 2, wherein the two spaced apart projections extend in the general direction of the air stream generated by the fan.

12. The dispenser of claim 2, wherein the two spaced apart projections are positioned in the air stream generated by the fan.

13. The dispenser of claim 1, wherein the guide is integral with the housing.

14. The dispenser of claim 1, wherein the guide comprises a wall member surrounding the opening.

15. The dispenser of claim 14, wherein the wall member is positioned entirely around the opening.

16. The dispenser of claim 1, wherein the guide includes a wall member positioned to surround a top portion of the wick.

17. The dispenser of claim 16 wherein the wall member is positioned entirely around the top portion of the wick.

18. The dispenser of claim 1, wherein the opening of the guide is positioned relative to the fan to position the wick in alignment with a rotational axis of the fan.

19. The dispenser of claim 1, wherein the predetermined dimension of the opening is greater than a dimension of the wick.

20. The dispenser of claim 1, including a fan blade of the fan having a length R measured from an axis of rotation of the fan to the farthest end of the fan blade away from the axis of rotation and wherein the predetermined dimension of the opening does not exceed 1.25 R.

21. The dispenser of claim 20, wherein the predetermined dimension of the opening does not exceed 1.1 R.

22. The dispenser of claim 20, wherein the predetermined dimension of the opening does not exceed 0.9 R.

23. The dispenser of claim 20, wherein the predetermined dimension of the opening does not exceed 0.7 R.

24. The dispenser of claim 20, wherein the predetermined dimension of the opening does not exceed 0.5R.

25. The dispenser of claim 1 wherein the wick has a dimension not to exceed 1.2 of a length R of a fan blade of the fan measured from an axis of rotation to a farthest end of the fan blade away from the axis of rotation.

26. The dispenser of claim 25, wherein the dimension of the wick does not exceed R.

27. The dispenser of claim 25, wherein the dimension of the wick does not exceed 0.8R.

28. The dispenser of claim 25, wherein the dimension of the wick does not exceed 0.6R.

29. The dispenser of claim 25, wherein the dimension of the wick does not exceed 0.4R.

30. The dispenser of claim 1, wherein the predetermined dimension of the opening is positioned generally transverse to an axis of rotation of the fan.

31. The dispenser of claim 1, wherein the dispenser operates at room ambient temperature.

32. The dispenser of claim 1, wherein the guide is adapted to position the wick within a cylindrical volume centered along an axis of rotation of the fan and having a radius which extends from the axis of rotation to the farthest extension of a fan blade of the fan.

33. The dispenser of claim 1 wherein the guide comprises a projection extending from a surface of the housing and positioned spaced apart from another surface of the housing, and the opening comprises a separation between the projection and the other surface of the housing.

34. The dispenser of claim 33 wherein the projection is spaced apart from a rotational axis of the fan in a direction transverse to a direction in which the wick is received into the opening.

35. A dispenser for a volatile liquid, comprising:
a housing;
a fan mounted to the housing to generate an air stream;
a guide associated with the housing provides at least one boundary in defining an opening in which the opening has a predetermined dimension to selectively receive a wick and to position the wick in alignment with the fan to immerse the wick into an air stream when the fan is activated, wherein the guide is integral with the housing, and wherein the guide comprises opposing sidewalls defining another opening of the housing.

36. A method for assembling a dispenser for a volatile liquid, comprising the steps of:
providing a fan mounted to a housing; and
providing a guide associated with the housing in which the guide includes a projection disposed on an inside surface of the housing that at least partly defines an opening having a predetermined dimension to selectively receive a wick and align the wick to be immersed in an air stream when the fan is activated.

37. The method of claim 36 including the step of inserting a wick into the opening to be aligned with the fan.

38. The method of claim 36 in which the step of inserting includes positioning the wick in alignment with an axis of rotation of the fan.

39. The method of claim 38 in which the step of inserting includes providing the predetermined dimension to be larger than a dimension of the wick.

40. The method of claim 36 includes providing the predetermined dimension of the opening not to exceed 1.25 of the length R of a fan blade of the fan measured from an axis of rotation of the fan to a farthest end of a fan blade away from the axis of rotation of the fan.

41. The method of claim 40 in which the step of providing includes providing the predetermined dimension of the opening not to exceed 1.1 R.

42. The method of claim 40 in which the step of providing includes providing the predetermined dimension of the opening not to exceed 0.9 R.

43. The method of claim 40 in which the step of providing includes providing the predetermined dimension of the opening not to exceed 0.7R.

44. The method of claim 40 in which the step of providing includes providing the predetermined dimension of the opening not to exceed 0.5R.

45. The method of claim 36, includes the step of providing the dimension of the wick not exceed 1.2 of the length R of a fan blade of the fan measured from an axis of rotation of the fan to a farthest end of the fan blade away from the axis of rotation.

46. The method of claim 43, includes the step of providing a, dimension of the wick not to exceed R.

47. The method of claim 43, includes the step of providing a dimension of the wick not to exceed 0.8R.

48. The method of claim 43, includes the step of providing a dimension of the wick not to exceed 0.6R.

49. The method of claim 43, includes the step of providing a dimension of the wick not to exceed 0.4R.

50. The method of claim 36 in which the step of providing a guide includes positioning the wick within a cylindrical volume centered along an axis of rotation of the fan and having a radius which extends from the axis of rotation to the farthest end of a fan blade from the axis of rotation of the fan.

51. The method of claim 36 including the step of providing the predetermined dimension of the opening in an orientation generally transverse to an axis of rotation of the fan.

52. The method of claim 36 wherein the dispenser operates at room ambient temperature.

* * * * *